US00PP21546P2

(12) United States Plant Patent
Dümmen

(10) Patent No.: US PP21,546 P2
(45) Date of Patent: Nov. 30, 2010

(54) ***PELARGONIUM* PLANT NAMED 'DUEPASALRE'**

(50) Latin Name: *Pelargonium peltatum*
Varietal Denomination: Duepasalre

(75) Inventor: Tobias Dümmen, Rheinberg (DE)

(73) Assignee: Capital Green Investments, Ltd., Grand Cayman (KY)

( * ) Notice: Subject to any disclaimer, the term of this patent is extended or adjusted under 35 U.S.C. 154(b) by 0 days.

(21) Appl. No.: 12/586,403

(22) Filed: Sep. 21, 2009

(51) Int. Cl.
*A01H 5/00* (2006.01)

(52) U.S. Cl. ..... Plt./332
(58) Field of Classification Search ..... Plt./332

See application file for complete search history.

*Primary Examiner*—Annette H Para
(74) *Attorney, Agent, or Firm*—C. A. Whealy

(57) ABSTRACT

A new and distinct cultivar of Ivy *Geranium* plant named 'Duepasalre', characterized by its upright to outwardly spreading plant habit; vigorous growth habit; freely basal branching habit; freely flowering habit; red purple-colored double flowers; and good garden performance.

1 Drawing Sheet

Botanical designation: *Pelargonium peltatum.*
Cultivar denomination: 'Duepasalre'.

BACKGROUND OF THE INVENTION

The present invention relates to a new and distinct cultivar of Ivy *Geranium* plant, botanically known as *Pelargonium peltatum*, and hereinafter referred to by the name 'Duepasalre'.

The new Ivy *Geranium* plant is a product of a planned breeding program conducted by the Inventor in Rheinberg, Germany. The objective of the breeding program is to create new vigorous Ivy *Geranium* plants with dark green-colored leaves and attractive flowers.

The new Ivy *Geranium* plant originated from a cross-pollination made by the Inventor in July, 2006 in Rheinberg, Germany of a proprietary selection of *Pelargonium peltatum* identified as code number F-01-13, not patented, as the female, or seed, parent with a proprietary selection of *Pelargonium peltatum* identified as code number F-18-08, not patented, as the male, or pollen, parent. The new Ivy *Geranium* plant was discovered and selected by the Inventor as a single flowering plant from within the progeny of the stated cross-pollination in a controlled greenhouse environment in Rheinberg, Germany in May, 2009.

Asexual reproduction of the new Ivy *Geranium* plant by vegetative terminal cuttings in a controlled greenhouse environment in Rheinberg, Germany since May, 2009, has shown that the unique features of this new Ivy *Geranium* plant are stable and reproduced true to type in successive generations.

SUMMARY OF THE INVENTION

Plants of the new Ivy *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duepasalre'. These characteristics in combination distinguish 'Duepasalre' as a new and distinct cultivar of Ivy *Geranium*:

1. Upright to outwardly spreading plant habit.
2. Vigorous growth habit.
3. Freely basal branching habit.
4. Freely flowering habit.
5. Red purple-colored double flowers.
6. Good garden performance.

Plants of the new Ivy *Geranium* differ primarily from plants of the parent selections in flower color as plants of the female parent selection have lilac-colored flowers and plants of the male parent selection have hot pink-colored flowers.

Plants of the new Ivy *Geranium* can be compared to plants of *Pelargonium peltatum* 'Duepared', disclosed in U.S. Plant Pat. No. 19,236. In side-by-side comparisons conducted in Rheinberg, Germany, plants of the new Ivy *Geranium* differed primarily from plants of 'Duepared' in flower color as plants of 'Duepared' had red-colored flowers.

BRIEF DESCRIPTION OF THE PHOTOGRAPH

The accompanying colored photograph illustrates the overall appearance of the new Ivy *Geranium* plant, showing the colors as true as it is reasonably possible to obtain in colored reproductions of this type. Colors in the photograph may differ slightly from the color values cited in the detailed botanical description which accurately describe the colors of the new Ivy *Geranium* plant. The photograph comprises a side perspective view of a typical flowering plant of 'Duepasalre' grown in a 10.5-cm container.

DETAILED BOTANICAL DESCRIPTION

The aforementioned photograph and following observations and measurements describe plants grown in Rheinberg, Germany in a glass- covered greenhouse during the summer and under conditions which closely approximate commercial production. During the production of the plants, day and night temperatures averaged 18° C. and light levels averaged 4,500 lux. Plants were pinched one time three weeks after planting. Plants had been growing for two months when the photograph and the description were taken. In the detailed description, color references are made to The Royal Horticultural Society Colour Chart, 1995 Edition, except where general terms of ordinary dictionary significance are used.

Botanical classification: *Pelargonium peltatum* 'Duepasalre'.

Parentage:

*Female, or seed, parent.*—Proprietary selection of *Pelargonium peltatum* identified as code number F-01-13, not patented.

*Male or pollen parent.*—Proprietary selection of *Pelargonium peltatum* identified as code number F-18-08, not patented.

Propagation:

*Type.*—By vegetative terminal cuttings.

*Time to initiate roots, summer.*—About five days at temperatures of 20° C.

*Time to initiate roots, winter.*—About seven days at temperatures of 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit: Freely branching.*

Plant description:

*General appearance.*—Upright to outwardly spreading plant habit; uniformly rounded; densely foliated.

*Growth and branching habit.*—Vigorous growth habit; freely basal branching habit with about three basal branches developing per plant.

*Plant height to top of flower umbels.*—About 20 cm.

*Plant height to top of foliar plane.*—About 13 cm.

*Plant width.*—About 24 cm.

*Lateral branches.*—Length: About 9 cm. Diameter: About 6 mm. Internode length: About 1.25 cm. Texture: Pubescent. Strength: Moderately strong. Color: Close to 143A.

Foliage description:

*Arrangement.*—Alternate; simple.

*Length.*—About 7.6 cm.

*Width.*—About 8.6 cm.

*Shape.*—Reniform.

*Apex.*—Acute.

*Base.*—Peltate.

*Margin.*—Crenate.

*Venation pattern.*—Palmate.

*Texture, upper surface.*—Pubescent; leathery.

*Texture, lower surface.*—Smooth, leathery.

*Color.*—Developing leaves, upper and lower surfaces: Close to 143A. Fully expanded leaves, upper surface: Close to 137A; venation, close to 144A. Fully expanded leaves, lower surface: Close to 143A; venation, close to 144A. Zonation pattern: Distinct. Distance from margin: About 2 mm. Width: About 1.5 cm. Color: Close to 187A.

*Petiole.*—Length: About 5.8 cm. Diameter: About 2.4 mm. Texture, upper and lower surfaces: Smooth, glabrous. Color, upper surface: Close to 139A. Color, lower surface: Close to 143A.

Flower description:

*Flower arrangement.*—Double rotate flowers arranged in rounded hemispherical umbels arising from apical leaf axils; umbels displayed above the foliage on moderately strong peduncles; flowers face upright to outward.

*Fragrance.*—Not detected.

*Quantity of flowers.*—Freely flowering habit; about nine flowers per umbel.

*Flowering season.*—Year-round under greenhouse conditions; in outdoor nurseries and gardens in Germany flowering is continuous from spring throughout the summer; plants begin to flower about eight weeks after planting.

*Flower longevity.*—Individual flowers last about five to seven days on the plant; flowers persistent.

*Umbel height.*—About 5.3 cm.

*Umbel diameter.*—About 8 cm.

*Flower diameter.*—About 5.4 cm.

*Flower depth (height).*—About 2.3 cm.

*Flower buds.*—Length: About 1.5 cm. Diameter: About 8 mm. Shape: Ovoid. Color: Close to 45B.

*Petals.*—Quantity per flower: About five or six. Length: About 2.6 cm. Width: About 2 cm. Shape: Obovate. Apex: Rounded. Base: Attenuate. Margin: Sinuate. Texture, upper and lower surfaces: Smooth, glabrous. Color: When opening, upper surface: Close to 57A. When opening, lower surface: Close to 44B to 44C. Fully opened, upper surface: Close to 57A. Fully opened, lower surface: Close to 43B to 43C; color becoming closer to 44B with development.

*Petaloids.*—Quantity per flower: About 10 to 15. Length: About 2.6 cm. Width: About 1.4 cm. Shape: Obovate. Apex: Rounded. Base: Attenuate. Margin: Sinuate. Texture, upper and lower surfaces: Smooth, glabrous. Color: When opening, upper surface: Close to 57A. When opening, lower surface: Close to 44B to 44C. Fully opened, upper surface: Close to 57A. Fully opened, lower surface: Close to 43B to 43C.

*Sepals.*—Quantity per flower: Five, arranged in a single whorl. Length: About 1.4 cm. Width: About 4.3 mm. Shape: Ensiform. Apex: Apiculate. Base: Attenuate. Margin: Entire. Color, upper and lower surfaces: Close to 144A.

*Peduncle (umbel stem).*—Length: About 7.5 cm. Diameter: About 3 mm. Strength: Moderately strong. Texture: Smooth, glabrous. Color: Close to 144A.

*Pedicel (individual flower stem).*—Length: About 2.4 cm. Diameter: About 1.5 mm. Strength: Moderately strong. Texture: Pubescent. Color: Close to 144A.

*Reproductive organs.*—Androecium: Stamen quantity per flower: About five to eight. Filament length: About 1.1 cm. Filament color: Close to 155D. Anther length: About 2 mm. Anther shape: Oval. Anther color: Close to 59A to 59B. Pollen amount: Moderate. Pollen color: Close to 28A. Gynoecium: Pistil quantity per flower: One. Pistil length: About 1 cm. Stigma shape: Parted. Stigma color: Close to 46A. Style length: About 2 mm. Style color: Close to 11B. Ovary color: Close to 144A.

*Seed/fruit.*—Seed and fruit development have not been observed.

Disease/pest resistance: Plants of the new Ivy *Geranium* have not been observed to be resistant to pathogens and pests common to Ivy *Geraniums.*

Garden performance: Plants of the new Ivy *Geranium* have been observed to tolerate rain, wind, and temperatures ranging from about 5° C. to about 40° C. and have demonstrated good garden performance.

It is claimed:

1. A new and distinct Ivy *Geranium* plant named 'Duepasalre' as illustrated and described.

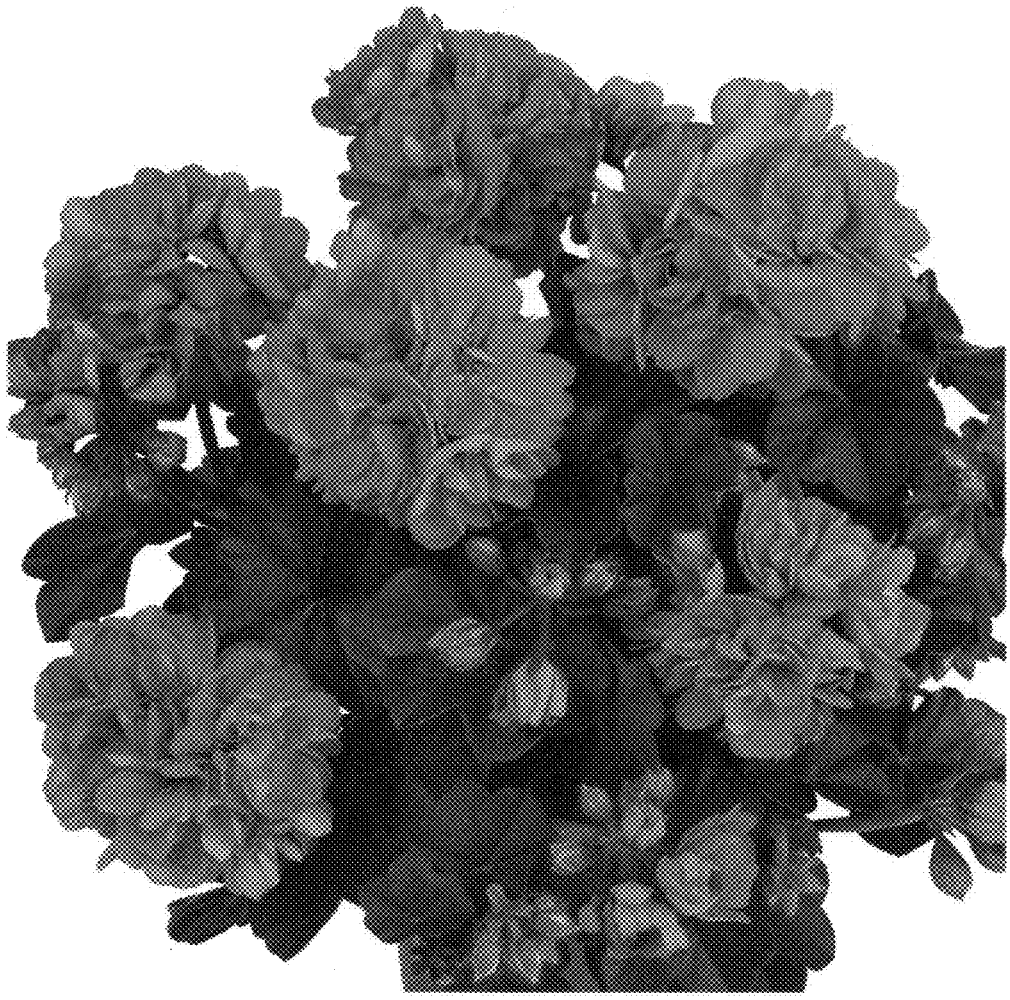

* * * * *